(12) United States Patent
Jallon et al.

(10) Patent No.: US 9,074,355 B2
(45) Date of Patent: Jul. 7, 2015

(54) DOMESTIC WATER RECYCLING APPARATUS AND FLUID CONTAMINATION DETECTION SYSTEM THEREFOR

(75) Inventors: Romain Jallon, Montreal (CA); Sebastien Blais-Ouellette, Laval (CA); Antoine Valette, Montreal (CA)

(73) Assignee: REVEECO INC., Montreal (CA)

( * ) Notice: Subject to any disclaimer, the term of this patent is extended or adjusted under 35 U.S.C. 154(b) by 964 days.

(21) Appl. No.: 12/996,385

(22) PCT Filed: Jun. 5, 2009

(86) PCT No.: PCT/IB2009/052399
§ 371 (c)(1),
(2), (4) Date: Dec. 4, 2010

(87) PCT Pub. No.: WO2009/147647
PCT Pub. Date: Dec. 10, 2009

(65) Prior Publication Data
US 2011/0146800 A1  Jun. 23, 2011

Related U.S. Application Data

(60) Provisional application No. 61/059,004, filed on Jun. 5, 2008.

(51) Int. Cl.
C02F 1/00 (2006.01)
A47K 3/022 (2006.01)
(Continued)

(52) U.S. Cl.
CPC . *E03B 1/04* (2013.01); *C02F 1/001* (2013.01); *C02F 1/32* (2013.01); *C02F 1/78* (2013.01);
(Continued)

(58) Field of Classification Search
USPC ........ 210/94, 456, 745; 4/596, 597, 602, 603, 4/604, 605, 612; 137/901, 1, 544
See application file for complete search history.

(56) References Cited

U.S. PATENT DOCUMENTS 3,435,209 A 3/1969 Keahl
4,055,496 A * 10/1977 Friedrich et al. ................ 210/87
(Continued)

FOREIGN PATENT DOCUMENTS

DE 4204209 8/1993
DE 10033479 A1 1/2002
(Continued)

OTHER PUBLICATIONS

The International Search Report for parent PCT application No. PCT/IB2009/052399, Dec. 10, 2009.
(Continued)

*Primary Examiner* — Nam Nguyen
*Assistant Examiner* — Richard Gurtowski
(74) *Attorney, Agent, or Firm* — J-TEK Law PLLC; Jeffrey D. Tekanic; Scott T. Wakeman

(57) ABSTRACT

A domestic water recycling system using a combination of an optical detector to detect certain smaller sized (non-filtered) contaminants and a filter to remove larger sized (filtered) contaminants provides an efficient wastewater recycling system. Optical detection of contaminants determines whether water is discharged or filtered and recycled. The optical detection system can use several discrete optical wavelengths that are passed through the fluid, and can determine a relative presence of the contaminants based on the resulting wavelength response. A recycling shower using optical detection, an electronically actuated directional device and pump and a controller allows for automatic recycling or discharging of water without requiring user input. The system may include a turbulence reduction baffle in a collection chamber, and a disinfection unit for the recycled water.

14 Claims, 7 Drawing Sheets

(51) Int. Cl.
  *E03B 3/18* (2006.01)
  *E03B 1/04* (2006.01)
  *C02F 9/00* (2006.01)
  *G01N 21/85* (2006.01)
  *E03C 1/00* (2006.01)
  *C02F 1/32* (2006.01)
  *C02F 1/78* (2006.01)
  *C02F 103/00* (2006.01)
  *G01N 21/94* (2006.01)

(52) U.S. Cl.
  CPC ........... *C02F 9/005* (2013.01); *C02F 2103/002* (2013.01); *C02F 2209/005* (2013.01); *C02F 2209/02* (2013.01); *C02F 2209/40* (2013.01); *E03B 2001/045* (2013.01); *G01N 21/85* (2013.01); *G01N 21/94* (2013.01); *G01N 2201/0627* (2013.01); *E03C 1/00* (2013.01)

(56) References Cited

U.S. PATENT DOCUMENTS

| | | | | |
|---|---|---|---|---|
| 4,059,529 A | * | 11/1977 | McGivern | ..................... 210/519 |
| 5,486,693 A | | 1/1996 | Achter et al. | |
| 5,630,987 A | * | 5/1997 | Briggs et al. | ..................... 422/82 |
| 2007/0222973 A1 | | 9/2007 | Hoshiko et al. | |
| 2010/0133200 A1 | * | 6/2010 | Gin et al. | ..................... 210/742 |

FOREIGN PATENT DOCUMENTS

| | | |
|---|---|---|
| EP | 1338709 | 8/2003 |
| EP | 1845363 A | 10/2007 |
| FR | 2907145 A | 4/2008 |
| WO | 2004/101902 | 11/2004 |
| WO | 2005/083188 | 9/2005 |
| WO | WO 2007 059051 A2 * 5/2007 | ............... E03C 1/044 |

OTHER PUBLICATIONS

The Written Opinion for parent PCT application No. PCT/IB2009/052399, Dec. 5, 2010.

The International Preliminary Report on Patentability for parent PCT application No. PCT/IB2009/052399, Dec. 5, 2010.

* cited by examiner

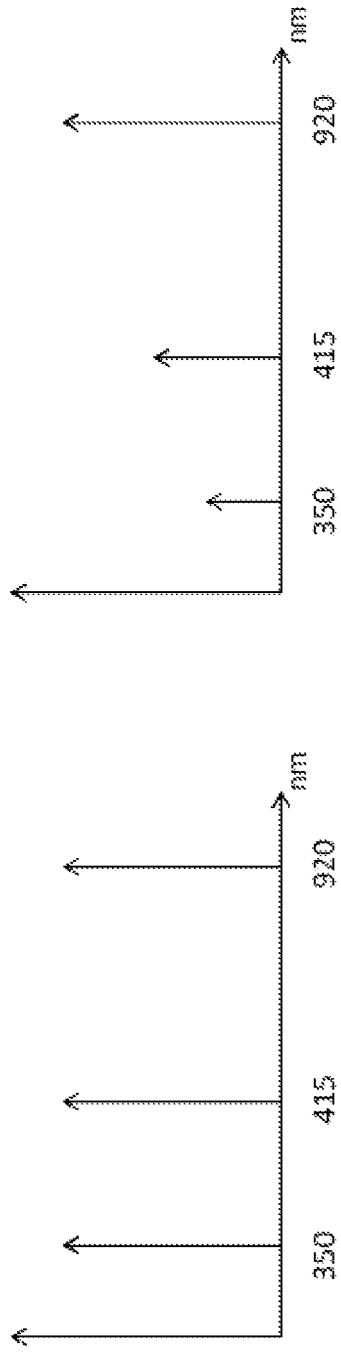
FIGURE 4A
FIGURE 4B
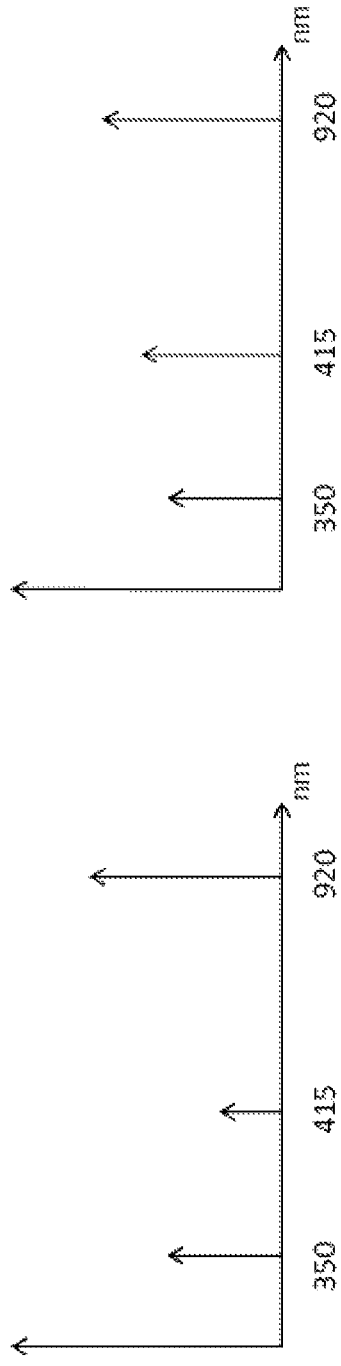
FIGURE 4C
FIGURE 4D

DOMESTIC WATER RECYCLING APPARATUS AND FLUID CONTAMINATION DETECTION SYSTEM THEREFOR

CROSS-REFERENCE

This application is the US national stage of International Patent Application No. PCT/IB2009/052399 filed on Jun. 5, 2009, which claims priority to U.S. Provisional Patent Application No. 61/059,004 filed on Jun. 5, 2008.

FIELD OF THE INVENTION

This invention relates generally to the field of detection and removal of contaminants in fluids and, more specifically, to a domestic water recycling apparatus using such detection.

BACKGROUND OF THE INVENTION

The detection and removal of contaminants in a fluid finds application across many fields, including the field of water consumption and recycling. In many parts of the world, clean water is becoming a scarce commodity. Water treatment to remove contaminants can be effective, but is often costly, or uses technology that is not readily available. One area of high water consumption is the household shower, in which water is continuously distributed from a showerhead and collected by a drain below. The water in the drain is discarded with other forms of wastewater, but is often less contaminated than wastewater from other sources, especially during times when no soap is being used. Moreover, the types of contaminants that enter the water in the shower are typically limited, and enter sporadically. As such, a large amount of the water entering a drain in a household shower is relatively clean.

Previous attempts at recycling showers involve manual user control to change the outflow direction of the used water to reuse the water when it is clean (WO 2004/101902), or have filtration means to filter and pump to recirculate all of the wastewater from the shower (WO 2005/083188). While effective to a certain extent, these methods are inherently limited in their ability to control the recycling of shower water with a high degree of efficiency or with a high degree of confidence regarding a true level of contamination of the used water.

In recycling shower systems of the prior art, removing certain particulate contaminants from recycled water was found to be an important issue. It would therefore be possible to design a shower that removes all particulate contaminants with a filter pore size smaller than the smallest contaminant. This system would, however, require a pump of significant power/energy input in order to force water through a filtering device of such small porosity and would not permit the removal of soluble contaminants.

SUMMARY OF THE INVENTION

It has been discovered that the combination of an optical detector that detects certain small sized (non-filtered) contaminants and a filter that removes large sized (filtered) contaminants can provide an efficient wastewater recycling system that overcomes drawbacks of prior art systems.

It is therefore an object of the present invention to provide a wastewater recycling system that optically detects specific (non-filtered) contaminants smaller than a predetermined filter pore size such that, when contaminants are not optically detected, water is filtered and recycled. Any contaminant larger that the filter pore size need not be optically detected whereas contaminants smaller than the filter pore are optically detected based on wavelength specific absorption/emission signatures.

It is another object of the present invention to provide an automatic recycling shower system that does not require user input other than temperature and flowrate which can, if desired, be manually selected by the user. In such a system, a directional device automatically directs water to either a recycling conduit or to an outflow conduit for discharge based on the presence of one or more non-filterable contaminants.

In accordance with the present invention, there is provided an apparatus for automatically recycling or discharging a fluid based on the presence of at least one contaminant comprising an optical contaminant detection device adapted to detect one or more contaminants in a fluid, a contaminant removal device for removing particulate matter from the fluid, a recycling conduit for recycling uncontaminated fluid from the contaminant removal device, an outflow conduit for discharging contaminated fluid, a directional device for directing fluid to one of the outflow conduit and the recycling conduit in response to contaminant detection by the optical contaminant detection device, and a controller receiving input from the detection device and sending output to the directional device for controlling the recycling or discharging of said fluid.

Also in accordance with the present invention, a domestic water recycling apparatus is provided that makes use of an optical detection system that detects the presence of one or more known contaminants in a fluid under test. The optical detection system uses a first optical source that outputs a first optical signal at a first wavelength that passes through the fluid under test. The first wavelength is a wavelength for which at least one of the contaminants has a characteristic absorption. A first optical detector is positioned to detect the first optical signal, and generates an electrical output signal indicative of the magnitude of the signal it detects. A second optical source is also provided that outputs a second optical signal at a second wavelength different than the first, the second optical signal also passing through the fluid under test. A second detector is positioned to detect the second optical signal once it has passed through the fluid under test, and it generates an electrical output indicative of the optical signal magnitude. The second wavelength is selected due to it being one of the wavelengths for which a second one of the contaminants has a characteristic absorption. Additional optical sources and detector pairs may be used to provide more information regarding the optical absorption characteristics of the fluid under test. In particular, a reference optical signal may be used that is at a wavelength that is not absorbed by any of the contaminants. Such a signal may be used together with the others as a baseline to determine whether attenuations of other optical signals are due to the presence of contaminants or to a source of diffusion, such as bubbles, in the fluid under test. The electrical output signals are all received by a controller that uses them to determine the presence of the contaminants in the fluid under test.

In an exemplary embodiment, the optical detection system is part of a domestic water recycling system for water that is output at a distribution point. Such a system may, for example, take the form of a recycling shower, where the distribution point is a showerhead. The system uses a collection chamber to collect used water that has originated from the distribution point. From the collection chamber, the used water may pass either to an outflow conduit for discarding water that is contaminated, or to a recycling conduit by which water that is not contaminated may be returned to the distribution point. A collection chamber should be understood as meaning any structure, device or apparatus that can receive and/or contain used water from a shower and includes a conduit, a pipe, a reservoir and a vessel. The system selects either the outflow conduit or the recycling conduit based on an optical inspection of the fluid under test (i.e., the water in the chamber) using the optical detection system. During normal operation of the system, water that is "contaminated" (i.e., is determined to contain a certain threshold level of one or more of the known contaminants as described above) is directed to the outflow conduit. Water that is not contaminated is directed to the recycling conduit.

As mentioned above, the optical detection system can use a plurality of optical sources and matching detectors to detect the relative presence of a plurality of different contaminants, each of which has an optical absorption characteristic that includes absorption for at least one of the wavelengths of the optical sources used. In the case of a recycling shower, for example, the known contaminants may be soap, urine and blood. Thus, each of these contaminants would have a known degree of optical absorption at the chosen wavelengths, and their presence would therefore be detectable due to relative attenuation of one or more of the optical signals.

Based on the outputs from the detectors, the controller of the system operates directional apparatus for directing the water in the chamber to either the outflow conduit or the recycling conduit. The directional apparatus may include an electronically actuated valve or one or more pumps. The system may also use a filtration apparatus that traps particulate matter from fluid passing from the chamber to the recycling conduit. The filtration apparatus may be located in a chamber separate from the detection chamber in which the water is examined by the optical detection apparatus. In addition, a filter cleaning system may be used that passes a cleaning solution through the conduits of the system and which may be operated to dislodge particulate matter accumulated by the filtration apparatus and discard it via the outflow conduit. The filter cleaning system may use a flow of water that passes from the recycling conduit to the chamber. In one embodiment, the recycling shower uses a baffle that deflects used water as it enters the chamber region and inhibits turbulence in the used water accumulating in the chamber. This reduces the presence of bubbles in the used water that might otherwise affect the transmission of the optical signals through the used water, and helps maintains a constant, stable flow of used water through the detection reservoir. A disinfection unit, such as an ultraviolet lamp, may also be used with the system to kill bacteria in the uncontaminated water returned to the distribution point.

In some embodiments of the present invention, when non-filtered contaminants such as soap, blood and urine are not detected but the optical detection capability is impeded by a significant amount of particulate matter (filtered contaminants) such as dirt, sand and hair, water is automatically discharged to the drain, thus ensuring proper filter efficiency.

In accordance with the present invention, there is also provided an automated method for reducing energy and fresh water consumption while taking a shower comprising the steps of collecting shower water from a shower drain and detecting the presence of certain contaminants using the optical absorption characteristics of the contaminants. Following detection, shower water will be discharged if contaminants are detected or recycled if contaminants are not detected. When water is recycled, it first passes through a filter of appropriate pore size to remove unwanted particulate contaminants. Water temperature is also adjusted using a combination of recycled and fresh water, thus returning a combined temperature adjusted water to a shower head.

BRIEF DESCRIPTION OF THE DRAWINGS

FIGS. 4A-4D are graphical views of the response of selected optical signal wavelengths to different contaminants in a fluid under test through which the optical signals are passed.

DETAILED DESCRIPTION OF THE INVENTION

Figure 1:
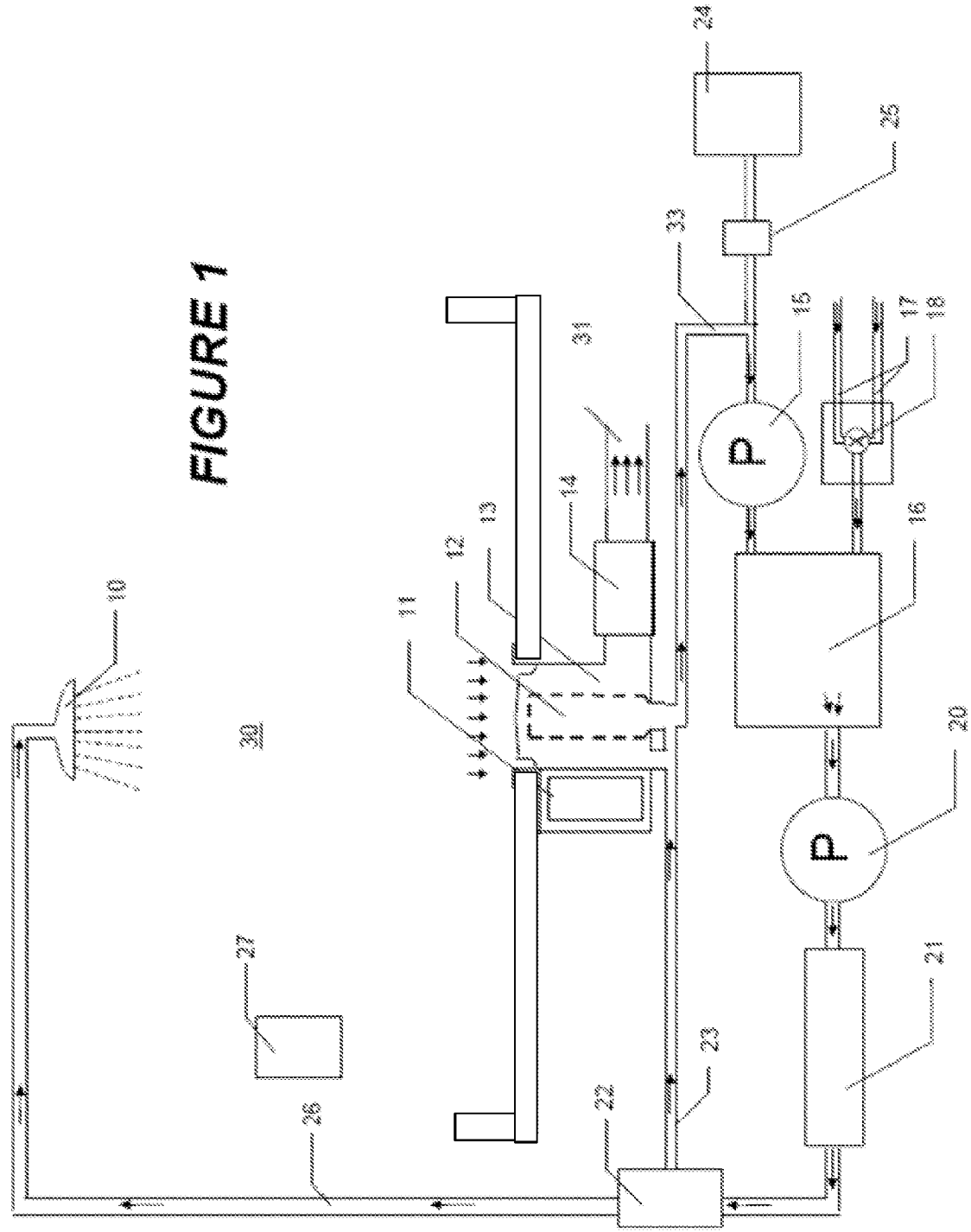
FIG. 1 is a schematic view of a recycling shower system according to the present invention.

Shown in FIG. 1 is a water recycling shower unit according to the present invention. Water enters the shower system via hot and cold water supply pipes 17. The valve apparatus 18 controls the relative flow of hot and cold water, respectively, from the pipes 17 to a mixing chamber 16. Water is then drawn from the mixing chamber by pump 20, and directed past disinfection unit 21 and valve 22 to conduit 26. The water is thereafter directed via the conduit 26 to showerhead 10, which distributes it within a space 30 below, where a user may be located.

Water output via the showerhead eventually passes through a drain to a collection chamber 13, along with any contaminants that may be been accumulated within the shower space 30. Located in the collection chamber 13 is a filtration apparatus 12, and access to two possible outflow conduits for the water collected therein. A first is via wastewater pipe 31, and the other is via recycling pipe 33, which directs clean water back to mixing chamber 16. The flow of water from the collection chamber 13 to the wastewater pipe is controlled by wastewater valve 14, and the flow to mixing chamber is controlled by pump 15. In particular, when the wastewater valve 14 is closed, and the pump 15 is activated, used water is directed from the collection chamber 13 to the mixing chamber 16. When the pump 15 is off, and the wastewater valve 14 is opened, used water is directed from the collection chamber 13 to the wastewater pipe 31. It will be appreciated by those skilled in the art that the directional device embodied by valve 14 can take other forms. For example, discharge of contaminated water can be achieved by reaching a certain overflow level in a collection chamber or conduit leading to a wastewater outlet. In this embodiment, activating a pump prevents overflow of "non-contaminated" water by reducing its level in the chamber/conduit whereas turning off a pump causes "contaminated" fluid to overflow. The reverse situation where an overflow stream is recycled and pumped stream is discharge is also possible.

It will also be appreciated by those skilled in the art that a directional device which directs fluid to both a recycling conduit and a discharge conduit can be variably adjusted such that only a portion of the collected fluid is recycled or discharged. This can be desirable, for example, when a certain level of a contaminant can be reached by recycling only a portion of the collected water and "diluting" the mixture to achieve the threshold concentration for a contaminant. Indeed, variably adjusting the recycle rate of collected water when only soap contaminants are detected can be advantageous.

The choice of which outflow port the water in the collection chamber will pass through is determined from examination of the water using an optical detection system 11, which is discussed in more detail hereinafter. The optical detection system 11 monitors the water for various contaminants, and provides a corresponding output signal to a controller 27. Depending on the information provided by the output signal, the controller 27 may open or close the electronically controlled valve 14 that leads to a wastewater pipe, and/or activate the pump 15 to direct the water back to the mixing chamber 16. The controller 27 may make use of any of a variety of known programmable control circuits, such as one or more EEPROMS and/or one or more commercially available microprocessors. Those skilled in the art will recognize that there are a number of different ways to implement the control structure described herein such that the controller 27 provides control of the shower based on user-controlled settings and signals received from the optical detection system 11. The controller generates signals to control the opening and closing of electronic valves 18 and 14, and to control the activation, deactivation and pumping speed of pumps 15 and 20. User settings include the activation and deactivation of the shower and a selection of the desired water flowrate and temperature, which affects the manner in which the controller operates valve apparatus 18 to introduce a relative amount of hot and cold water to the mixing chamber 16. In one embodiment of the invention, the controller operates the clean water supply pipes 17 to add additional hot water to the water in the mixing chamber 16, which may be cooler than desired due to recycled water having undergone a reduction in temperature. In addition, a temperature sensor may be located in the mixing chamber which provides an output signal to the controller 27 for use in determining whether to add hot or cold water to the mixing chamber in order to achieve a desired temperature. The controller also controls valves 22 and 25, as is discussed in more detail below. It will be appreciated by those skilled in the art that when the system operates in recycling mode for long periods of time and a significant amount of hot water is added to adjust the temperature, it may be desirable to have an overflow valve to discharge a volume of water which exceeds the containment capabilities of the system.

Figure 2:
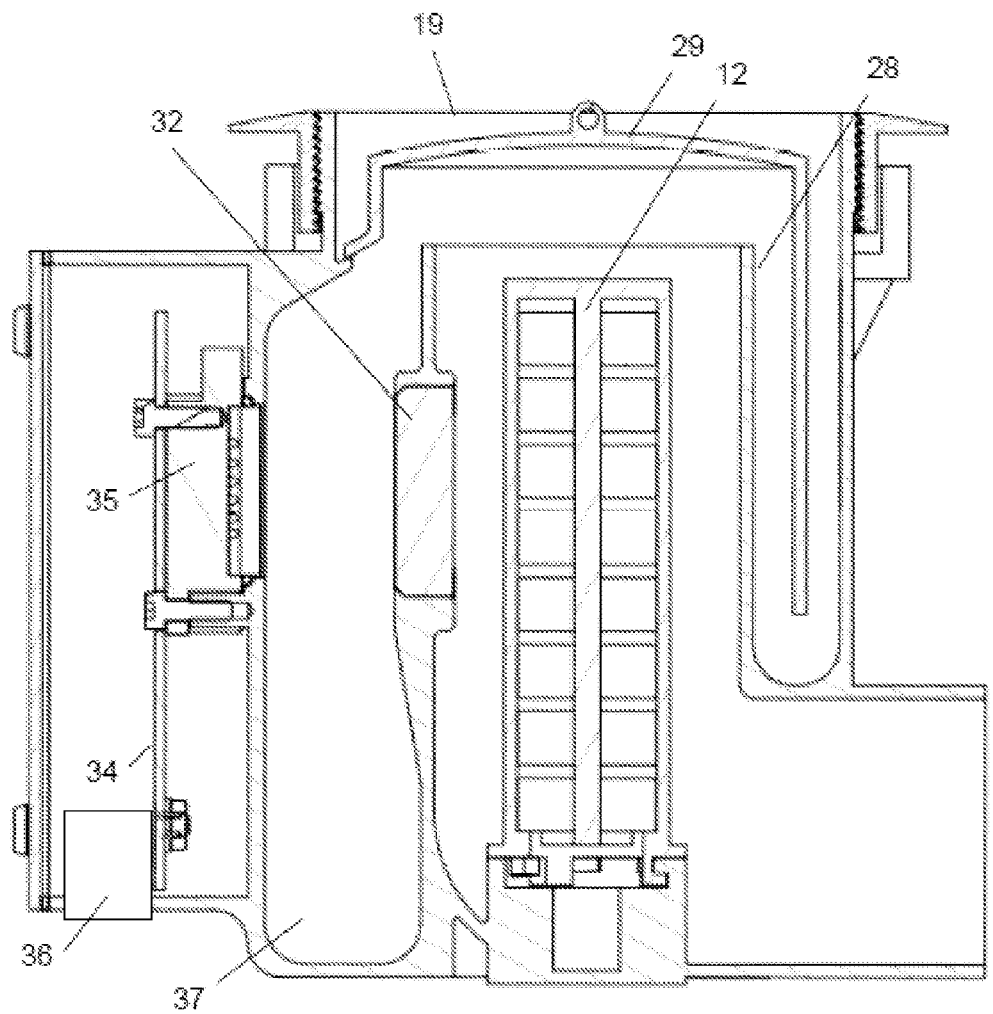
FIG. 2 is an isolated view of a collection chamber section of a system such as that of FIG. 1.

A cross-sectional view of the collection chamber 13 is shown in FIG. 2. The drain opening 19 allows the passage of water from the shower into the collection chamber 13. A filter housing cover 29 prevents passage of the water directly into the filter housing, directing it instead to a detection reservoir 37 that surrounds the filter housing 28. As water flows through the drain, it collects in the reservoir 37, and the water level rises until it reaches the top of the reservoir 37, which is open to the filter housing. Located adjacent to one section of the reservoir 37 is the optical detection apparatus, which includes a detection unit 35 and a reflector 32. The detection unit 35 and the reflector 32 are positioned opposite each other with a portion of the reservoir 37 between them. This allows optical signals from the detection unit to pass through water in the reservoir 37, be reflected by the reflector, and return to the detection unit. Thus, water filling the reservoir 37 undergoes an optical inspection before reaching the interior of the filter housing. Notably, the filter housing cover 29 also serves as a baffle, minimizing turbulence in water entering the detection reservoir 37. Such turbulence might otherwise create numerous bubbles in the used water that could impede transmission of optical signals through the liquid.

The optical detection system uses multiple wavelengths of light that pass through the water in the reservoir 37, are reflected by the reflector and detected back at the detection unit. The relative absorption, or extinction, of light at these different wavelengths is indicative of certain contaminants that may be present in the water. An output signal from the detection unit is therefore sent to the controller 27 which, in turn, provides signals to the pump 15 and the wastewater valve 14 to effect either a recycling of the water or a dumping of the water into the wastewater pipe 31. In this embodiment, the detection unit is mounted to a printed circuit board 34 that includes a connector 36 for making power and signal connections to the controller 27.

If, based on the detection signal received, the controller 27 determines that the water in the collection chamber should be dumped, the wastewater valve 14 is opened, and the water that passes into the filter housing 28, prior to its filtration, is allowed to drain into the wastewater pipe under the force of gravity. However, if the controller determines that the water should be recycled, the wastewater valve 14 is closed, and the pump 15 is activated. The force of the pump pulls water from the filter housing through the filter element and into the recycling pipe 33, delivering it to the mixing chamber 16. As the water passes through the filter element, particulates in the water are trapped by the filter and thereby removed from the water being recycled. In the present embodiment, the filter may use a water filter cartridge of a desired porosity. Moreover, the filter cartridge may be made manually removable from the filter housing, such that a user may change the filter periodically. The filter housing cover 29 may be removed to expose the filter housing, and the filter cartridge lifted out of the housing and replaced with a new cartridge. In the exemplary embodiment, the filter cartridge has a pore size of less than 50 μm, although those skilled in the art will recognize that different pore sizes may be used as well.

In the current embodiment, which is specifically directed to a recycling shower, the optical detection system is configured to detect certain specific contaminants. To accomplish this, the optical detection system relies on the absorption of specific optical wavelengths by components of the water being examined. This may be done using multiple light source/detector pairs, each of which is configured for a different desired wavelength. An example arrangement is shown in FIG. 3.

Figure 3:
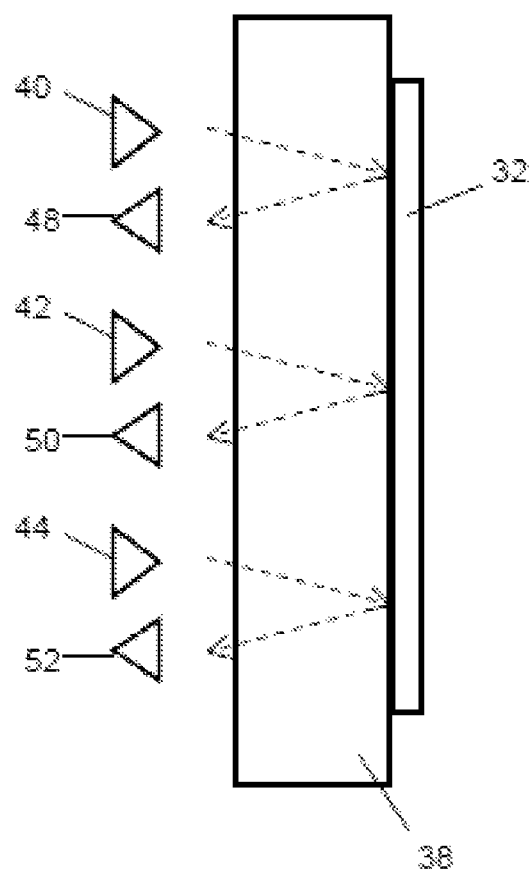
FIG. 3 is a schematic view of an optical detection apparatus that may be used with a system such as that shown in FIG. 1.

In FIG. 3, three sets of source/detector pairs are shown adjacent to a liquid receptacle 38 within which a liquid to be examined may reside. This receptacle 38 may be, for example, a section of the detection reservoir 37 shown in FIG. 2. Adjacent to the liquid receptacle of FIG. 3 are three light sources which, in this embodiment, are light-emitting diodes (LEDs) 40, 42, 44. Each of the LEDs has a different characteristic wavelength, and each has an output directed through a transparent barrier of the liquid receptacle 38. In this embodiment, LED 40 has a characteristic wavelength of 350 nm, LED 42 has a characteristic wavelength of 415 nm and LED 44 has a characteristic wavelength of 920 nm. The outputs of each of the LEDs are directed through the liquid in the receptacle 38 toward the reflector 32 located on the opposite side.

The mirror used with the present invention may be a concave mirror, which reflects the light from the LEDs at a predetermined angle. This allows for a desired angular reflection of light between the LEDs and detectors while maintaining them on a parallel surface, thereby removing the need for precise angular positioning of each device. Based on the reflection angle, and the separation of the LEDs and the mirror, a returning optical signal arrives to a position adjacent to its original LED source. Located at this position, for each of the wavelengths, is an optical detector that is sensitive to the wavelength in question. In particular, detector 48 is paired with LED 40, detector 50 is paired with LED 42 and detector 52 is paired with LED 44. The magnitude of the signals detected by each of the detectors is therefore indicative of the extent to which the optical energy of those signals was lost between the source and the detector positions. Losses result from absorption or refraction of the optical signal, and may provide information regarding the content of the liquid. Notably, the different wavelengths each respond differently to a particular contaminant of interest. For example, in the shower application of FIGS. 1 and 2, one may be interested in the contaminants typical of shower wastewater, such as urine, blood and soap. Each of these contaminants has a different absorption characteristic in that different optical wavelengths are absorbed to a different degree by each contaminant. As such, the detection of optical signals of different wavelengths that are passed through the liquid gives an indication of which contaminants may be present in the liquid, due to their relative degree of attenuation.

The optical detection system of the present invention is used to identify the relative presence and quantity of specific contaminants in the liquid being monitored. An example of this detection is shown in FIGS. 4A-4D, each of which is a graph of the magnitude of optical signals as detected by the detection system after passing through the liquid under test, given different contaminants contained therein. In the example of a recycling shower such as that shown in FIG. 1, the liquid under test is used water from the shower, and the contaminants of interest, therefore, may be urine, blood and soap, as mentioned above. To detect these contaminants, the optical sources are chosen to radiate, respectively, at certain absorption wavelengths of these materials, namely, 350 nm, 415 nm and 920 nm.

FIG. 4A shows the signal output for water that is clean, i.e., free of the target contaminants. As shown, the magnitudes of each of the measured wavelengths are essentially equal, as each of the wavelengths passes relatively easily through the clean water. FIG. 4B shows the wavelength response for water that has been contaminated by urine. As shown, the absorption characteristics of the contaminant result in a significant attenuation of light at the 350 nm wavelength, a moderate attenuation of light at the 415 nm wavelength, and little or no attenuation at the 920 nm wavelength. A different wavelength response is shown in FIG. 4C, which results from water contaminated by blood. In this response, there is a significant attenuation of light at the 415 nm wavelength, a moderate attenuation at the 350 nm wavelength, and a slight attenuation at 920 nm. Finally, FIG. 4D shows the wavelength response for water contaminated with soap. In this case, there is a moderate attenuation of the signals at 350 nm and 415 nm, and a slight attenuation at the 920 nm wavelength.

Figure 5:
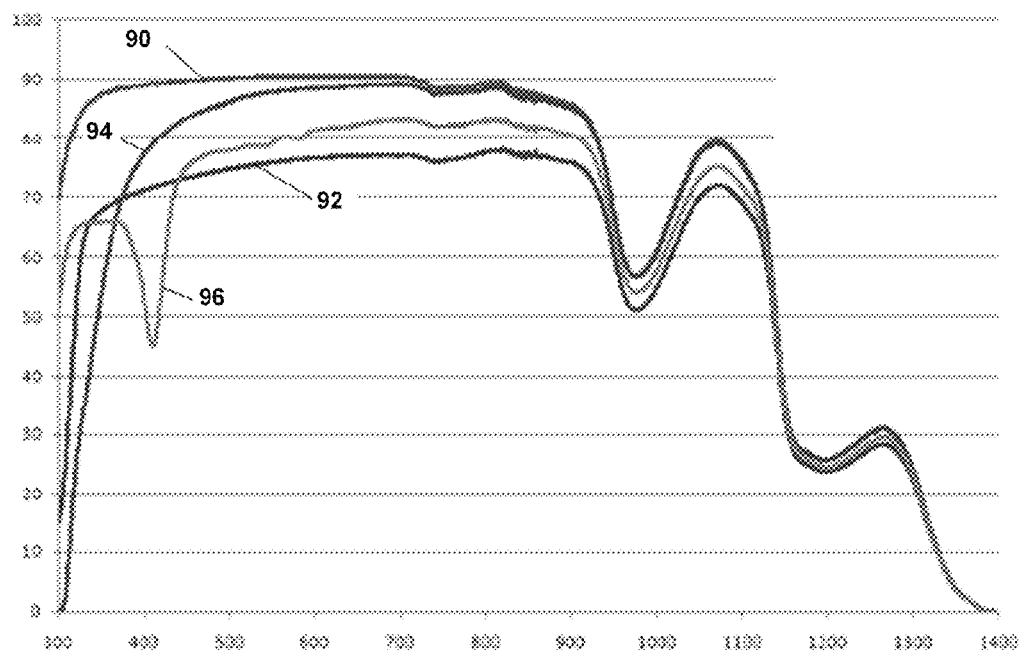
FIG. 5 is a graphical view of the wavelength response curves for multiple contaminants overlaid in a single graph.

As can be seen from FIGS. 4A-4D, the different wavelength characteristic responses caused by the different contaminants can be used to make a determination of the degree of contamination of the liquid being examined, in this case wastewater from the shower. The wavelength characteristics of FIGS. 4A-4D may also be better understood in combination with the graph of FIG. 5, which shows the transmission of different light wavelengths through water contaminated with different substances. The four curves shown in the figure correspond, respectively, to "clean" water (labeled 90), water contaminated with soap (labeled 92), water contaminated with urine (labeled 94) and water contaminated with blood (labeled 96). Viewing these curves simultaneously, it can be seen how they deviate from one another at different wavelengths, thereby allowing the distinction between different contaminants in a liquid under test.

Figure 6:
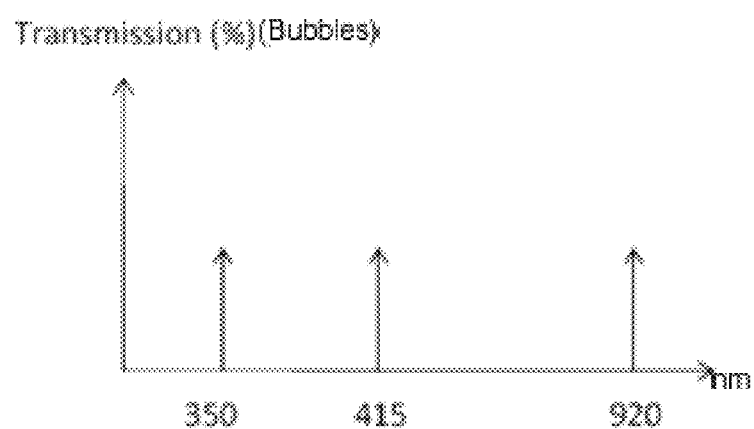
FIG. 6 is a graphical view of the response of selected optical signal wavelengths to the presence of bubbles in a fluid under test through which the optical signals are passed.

In addition to detecting the presence of specific contaminants, the present invention also provides for the identification of an overall reduction of optical transmission resulting from bubbles in the liquid. FIG. 6 shows the response of the three wavelengths discussed above to the presence of bubbles in contaminant-free water under test. As shown, the bubbles cause an attenuation of the optical signals, but the attenuation is approximately equal for each. However, this attenuation can be distinguished from attenuations caused by the presence of contaminants, and the controller may continue to recycle the water in the presence of such signal attenuation, provided the attenuation pattern indicates that it was not caused by one or more contaminants. Conversely, because the reduction in magnitude from bubbles is equal at all of the wavelengths, the detection of specific contaminants may be based on a relative attenuation between the different wavelengths, rather than on an absolute amount. Thus, if each of the detected wavelengths suffers attenuation due to bubbles, but the overall relative attenuation between the wavelengths is still indicative of a wavelength response that is particular to a particular contaminant, the controller determines that the contaminant is present and discard the water.

In the foregoing embodiment, the 920 nm wavelength does not respond much to the presence of the target contaminants, but may be useful in the capacity of a "baseline" detection wavelength in that it reacts (like the other wavelengths) to an overall reduction in optical transmission through the water. However, those skilled in the art will recognize that such a baseline detector is not an absolute necessity for the invention, and that contaminant detection may use only the wavelengths that show a significant response to the presence of the target contaminants. Thus, the example above could operate with just the 350 nm and 415 nm source/detector pairs.

The operation of a recycling shower such as is shown in FIG. 1 has been described above, including the use of a filtration apparatus to remove particulate matter from water being returned from the collection chamber 13 to the mixing chamber 16. In one embodiment of the present invention, the system may also include a filter cleaning system to provide for the automatic removal of much of the debris that may have been trapped by the filtration apparatus 12. In the path from the mixing chamber 16 to the showerhead 10 is a valve 22 that allows the direction of water from the mixing chamber either to conduit 26 or to conduit 23. The opposite end of conduit 23 is in fluid communication with the interior (i.e., the "clean" side) of the filter cartridge of filtration apparatus 12.

When the shower is not in use, the pumps 15 and 20 may be activated and the system cleaned using a cleaning/disinfecting solution stored in cleaning solution chamber 24. During the operation of the pumps, a valve 25 may be opened to allow the cleaning solution to mix with the water being cycled by pumps 15 and 20. This allows for the cleaning and disinfecting of the interior surfaces of the system. After a first cleaning phase (with a duration of, for example, twenty seconds) during which the water and cleaning solution pass through the primary water conduits of the system, a second phase may also be used. In this second phase, valve 22 is switched to direct water delivered by the pump 20 through conduit 23 to the filtration apparatus. At this time the pump 15 is deactivated so that there is no flow of water through the recycling conduit 33. Instead, under the force of the pump 20, the water and remaining cleaning solution arriving at the filter cartridge are forced through the filter in a direction opposite to that of its normal operation. During this phase, the wastewater valve 14 is opened, and the water forced through the filter cartridge is discarded, along with any particulate matter that it has dislodged from the filter, thereby providing a cleaning of the filter cartridge and extending its useful life. This process may be continued until the mixing chamber 16 has been emptied.

In the exemplary embodiment of the invention, the filter cleaning process is automated, and controlled by controller 27. At a time when the shower is not in use, the controller may initiate the filter cleaning operation, providing the control signals to activate pumps 15, 20, valve 22, valve 14 and valve 25. The timing of the operation and corresponding control of the pump and valves involved would be such as to provide a brief cleaning of the filter and, after closing the cleaning solution valve 25, sufficient operation of the pump 20 to ensure that the particulate matter and cleaning solution are removed from the system through wastewater conduit 31 before shutting off the pump 20 and returning the valves 22 and 14 to their default positions.

Another feature of the exemplary embodiment is the use of a disinfection unit 21 shown in FIG. 1. This unit may be used to kill bacteria present in the water drawn from the mixing chamber 16, and may take the form, for example, of an ultraviolet lamp that, in this example, is 25 Watts. The radiation from the lamp would be sufficiently strong to make it toxic to many forms of common bacteria, thereby providing a degree of disinfection to the water recycled through the system. It should be noted that the disinfection unit can also be placed in fluid communication with recycling pipe 33 such that only water recycled from the shower is disinfected. The location of the disinfection unit can depend on the type disinfection unit. If the disinfection unit is a UV lamp, it can be advantageous to have a lamp that conforms to the shape of conduit 26 to insure maximal surface area for the UV lamp. In other cases such as ozone and/or oxidant in situ generation or external addition, it can be advantageous to treat the smallest volume of fluid due to the upscaling cost of such units and/or for achieving concentration requirements of the added chemicals in the water. Furthermore, when chemical disinfectants are added, it may be advantageous to do so as early as possible in the process to insure effective treatment time and to insure that residual chemicals are not released in significant amount at the distribution point/shower head. If heat is used to disinfect the recycled water, it would be advantageous to have the disinfection unit as early as possible in the process and upstream from the mixing chamber to allow water temperature control.

In some embodiments of the present invention, and specifically when applied to a recycling shower system, such a system can be configured to allow easy access to certain system components such as a filter which can require maintenance. Easy access can be achieved by placing the recycling system under a shower space 30 such that the shower floor is also a platform or cover for the recycling shower components. Placing the recycling shower system under a shower space 30 is ideal as the shower drain can empty into a collection chamber by gravity without requiring extra energy input from a pump for example. Embodiments of the easy access device includes, but should not be understood as being limited to: placing the recycling shower system under shower space 30 as a slide-in cassette/drawer which can be easily inserted and removed, or removing a platform 61 to expose system components. Although a totally new recycling shower system can be designed according to present invention, an existing shower may also be adapted (retrofitted) to include recycling capability according to the present invention.

Figure 7:
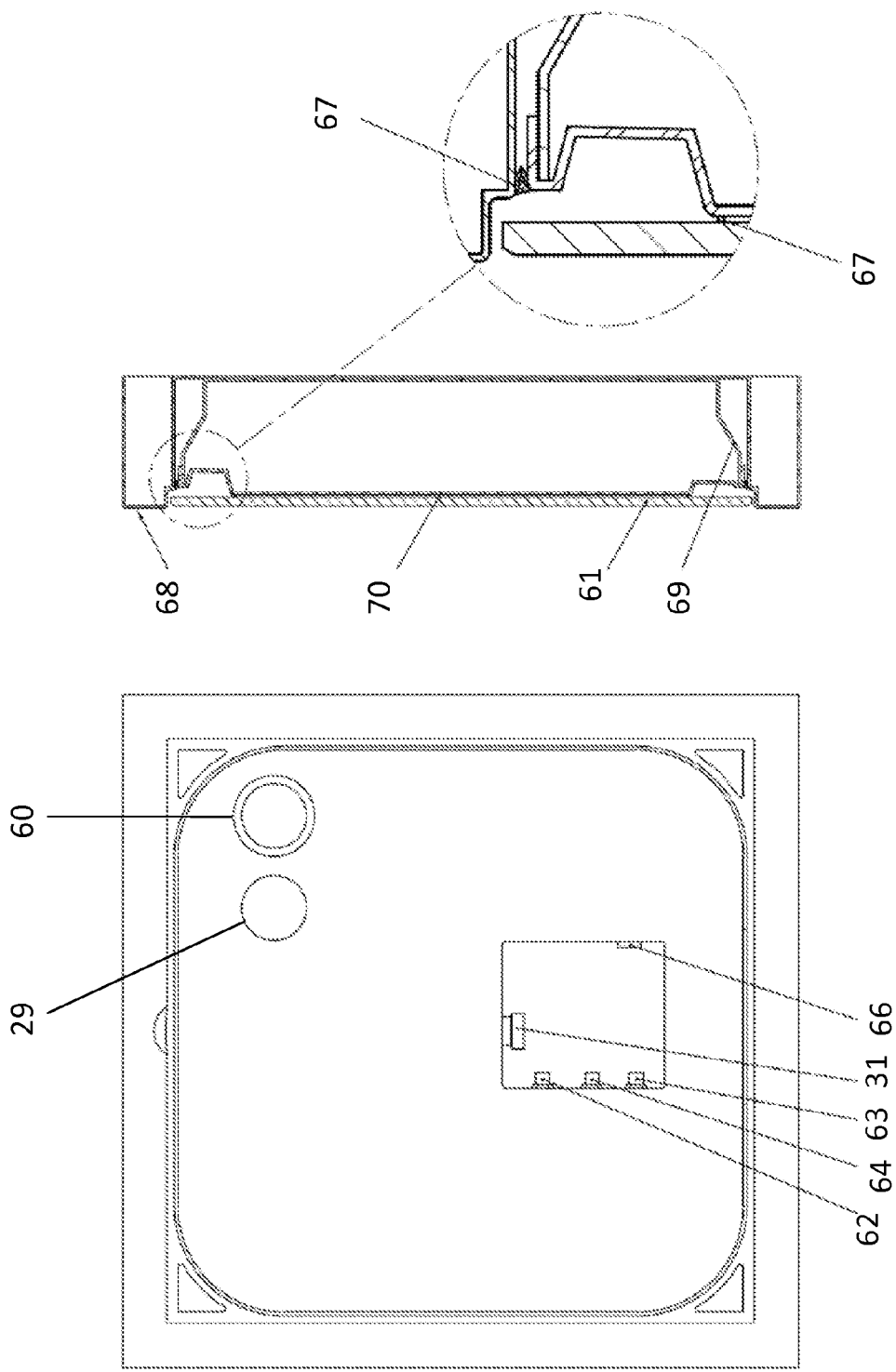
FIG. 7 is a schematic top and side view of a recycling shower system including a platform for easy access to system components

FIG. 7 depicts a top and side view of a recycling shower system with easy-access design. In such an embodiment, removing platform 61 allows access to filter housing cover 29 and detector housing cover 60. Furthermore, removing the platform 61 exposes hot 63, cold 62 and temperature-adjusted 64 water connectors, the evacuation drain 31 as well as the electrical connection 66 to the recycling shower system. A shower system according to the present embodiment includes a contour receiver 68 for receiving a recycling shower system. This recycling shower system includes a body 69 comprising most system components upon which a receiver 70 can be placed for protection purposes. Sealing joints 67 can be applied between the contour receiver 68 and the receiver 70 and prevent water infiltrations to the bathroom floor.

Figure 8:
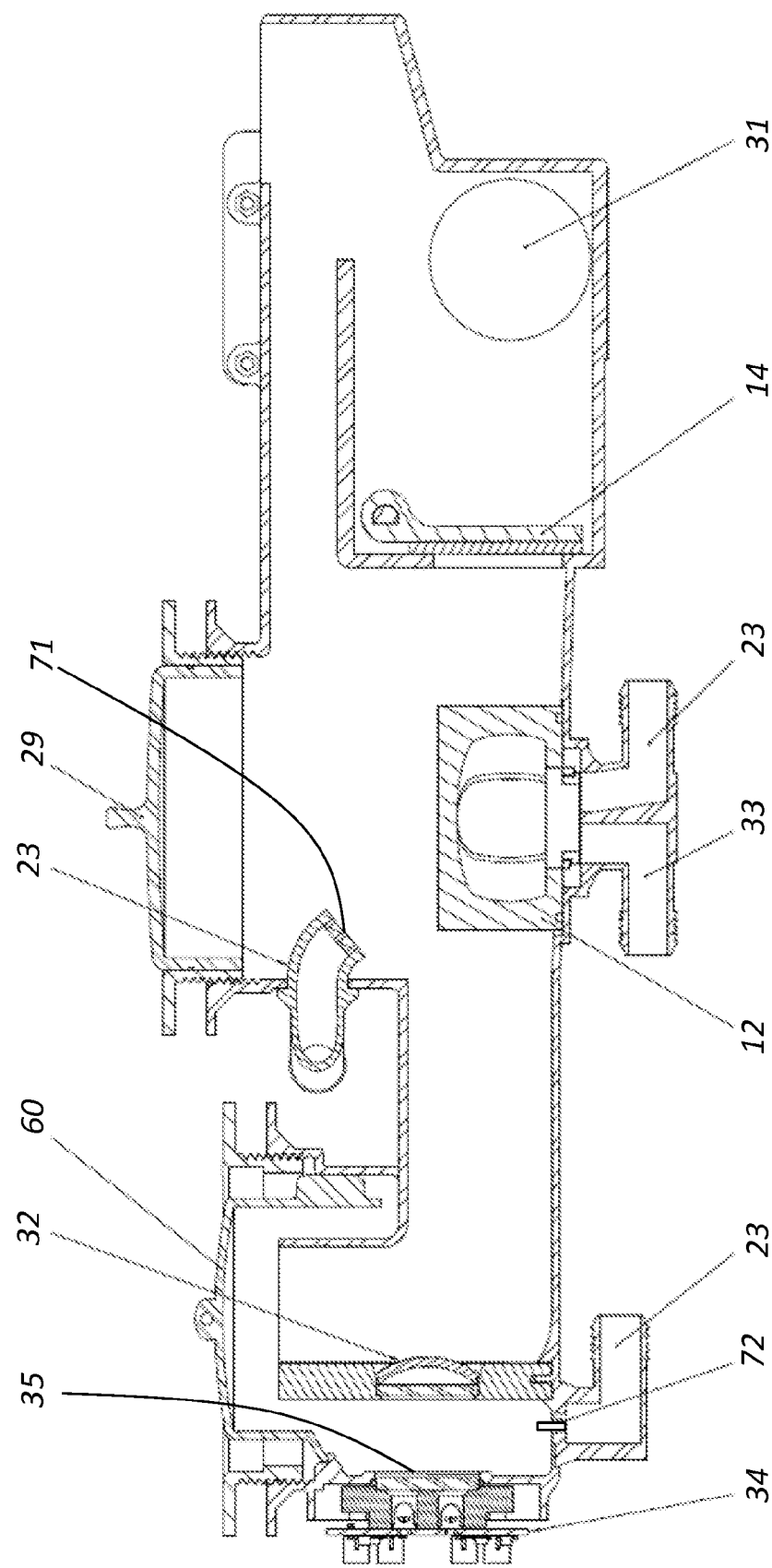
FIG. 8 is an isolated side view of a collection chamber section of a recycling shower system.

FIG. 8 is an isolated cross-sectional side view of the embodiment of FIG. 7 excluding platform 61. The filter housing cover 29 can be removed to expose the filter and the detector housing 60 can be removed to expose the optical detector. Water is discharged or evacuated to a wastewater pipe 31 when the directional valve 14 is open and water passes through filter 12 and is recycled through recycling conduit 33 when valve 14 is closed.

Three important aspects for automated cleaning of the recycling shower system are shown in FIG. 8. An internal cleaning conduit 23 is shown and its function has been described above as being adapted to direct water to the internal surface of the filter 12. Additionally, conduit 23 can be split to direct water to an external filter cleaning nozzle 71 such that the filter is cleaned from both the clean side (internal) to detach particulate matter from the filter and the dirty side (external). A nozzle 71 is adapted to spray the filter over its entire external surface. Another nozzle 72 is adapted to spray water or a liquid cleaning solution onto the surface of the optical detector 35 and the reflector 32 in order to remove any contaminant buildup on such surfaces. In order to maximally benefit from the nozzles, it may be advantageous to use this cleaning system when no water is present (i.e. after the system has been emptied or flushed) such as after individual use. Other nozzles can also be used to spray the various components of this device likely to accumulate particulate matter that will not be effectively removed during normal operation of by the backwash mechanism.

While the invention has been shown with reference to a preferred embodiment thereof, it will be recognized by those skilled in the art that various changes in form and detail may be made herein without departing from the spirit and scope of the invention as defined by the appended claims. In particular, the optical detection of contaminants in liquids has been discussed herein in the context of a recycling shower, but those skilled in the art will recognize that such a detector may be used in a wide variety of other applications. Moreover, specific wavelengths have been used in the foregoing embodiments, but the choice of wavelengths may depend on the specific application and the specific contaminants of interest. The specific components being used may also be varied without deviating from the crux of the invention. Finally, the monitoring of shower wastewater is only one possible application involving "domestic" water, and other types of supply waters, such as well water, lake water and other wastewaters may be monitored in a similar manner.

What is claimed is:

1. An apparatus for automatically recycling or discharging a fluid based on the presence of at least one contaminant comprising:
    an optical contaminant detection device configured to detect at least first and second contaminants in the fluid, the optical contaminant detection device comprising:
        a first optical source that outputs a first optical signal at a first wavelength that passes through at least a portion of the fluid under test, the first wavelength being among a set of wavelengths for which at least the first contaminant has a characteristic absorption;
a first optical signal detector positioned to detect the first optical signal, the first detector generating a first electrical signal indicative of a magnitude of the detected first optical signal;
a second optical source that outputs a second optical signal at a second wavelength different from the first wavelength that passes through at least a portion of the fluid under test, the second wavelength being among a set of wavelengths for which at least the second contaminant has a characteristic absorption;
a second optical signal detector positioned to detect the second optical signal, the second detector generating a second electrical signal indicative of a magnitude of the detected second optical signal; and
a controller that receives the first and second electrical signals and determines therefrom the relative presence of the first and second contaminants in the fluid under test, wherein the identification of a relative wavelength response is made independent of the absolute magnitudes of the detected optical signals;
a contaminant removal device for removing particulate matter from the fluid;
a recycling conduit for recycling uncontaminated fluid from the contaminant removal device;
an outflow conduit for discharging contaminated fluid;
a directional device for directing fluid to the outflow conduit and the recycling conduit in response to contaminant detection by the optical contaminant detection device; and
a controller receiving input from the detection device and sending output to the directional device for controlling the recycling or discharging of the fluid.

2. An apparatus according to claim 1 wherein the directional device is configured to direct fluid to the outflow conduit when optical detection of the contaminants is impeded by particulate matter.

3. An apparatus according to claim 1 wherein the optical contaminant detection device further comprises a reflector located to a side of the fluid under test opposite the first optical source and the second optical source, and wherein the optical signals are reflected by the reflector such that they each pass through the fluid under test a second time.

4. An apparatus according to claim 1 wherein the contaminant removal device comprises a filter of 50 micron pore size.

5. An apparatus according to claim 4 wherein the optical contaminant detection device is disposed upstream from the filter such that non-filterable contaminants are prevented from entering the recycling conduit.

6. An apparatus according to claim 4 wherein the filter is located in a chamber separate from a detection reservoir in which fluid is examined by the optical contaminant detection device.

7. An apparatus according to any one of claim 4 further comprising a filter cleaning system configured to allow passage of at least one fluid or cleaning solution from the recycling conduit to a collection chamber, such that particulate matter accumulated by the filter is dislodged and discarded via the outflow conduit.

8. An apparatus according to claim 1 wherein the directional device comprises an electronically-actuated valve.

9. An apparatus according to claim 1 further comprising a collection chamber having a baffle configured to deflect fluid as it enters the collection chamber, the baffle being configured to inhibit turbulence in the fluid accumulating in the collection chamber.

10. An apparatus according to claim 1 further comprising a disinfection unit configured to kill bacteria in the recycled fluid, the disinfection unit comprising at least one of a UV lamp, an oxidant or ozone generator, a chemical or bactericide dispenser, and a heater.

11. A method for reducing energy and fresh water consumption while taking a shower comprising the steps of:
collecting shower water in a collection chamber,
detecting the presence of at least first and second contaminants using optical absorption characteristics of the contaminants;
actuating a directional device based on optical detection of said contaminants such that contaminated water is directed to a discharge conduit and non-contaminated water is directed to a recycling conduit, wherein recycled water first passes through a filter to remove particulate contaminants;
controlling said directional device with a controller receiving input from first and second optical signal detectors;
adjusting the temperature of said water using a combination of recycled and fresh water, and returning a combined temperature adjusted water to a shower head, wherein the controller receives input from a temperature sensor; and
wherein detecting the presence of the at least first and second contaminants comprises:
outputting a first optical signal from a first optical source at a first wavelength that passes through at least a portion of the water under test, the first wavelength being among a set of wavelengths for which at least the first contaminant has a characteristic absorption;
detecting the first optical signal using the first optical signal detector that generates a first electrical signal indicative of a magnitude of the detected first optical signal;
outputting a second optical signal from a second optical source at a second wavelength different from the first wavelength that passes through at least a portion of the water under test, the second wavelength being among a set of wavelengths for which at least the second contaminant has a characteristic absorption;
detecting the second optical signal using the second optical signal detector that generates a second electrical signal indicative of a magnitude of the detected second optical signal; and
receiving the first and second electrical signals in the controller that determines therefrom the relative presence of the first and second contaminants in the water under test, wherein the identification of a relative wavelength response is made independent of the absolute magnitudes of the detected optical signals.

12. An apparatus according to claim 1, wherein the optical contaminant detection device is configured to detect the at least the first and second contaminants based on wavelength specific absorption/emission signatures of the contaminants.

13. An apparatus according to claim 1, wherein the first and second contaminants are selected from the group consisting of urine, blood and soap.

14. A method according to claim 11, wherein the first and second contaminants are selected from the group of urine, blood, and soap.

* * * * *